(12) United States Patent
Hegeman et al.

(10) Patent No.: US 10,393,683 B2
(45) Date of Patent: Aug. 27, 2019

(54) CONICAL COLLIMATOR FOR X-RAY MEASUREMENTS

(71) Applicant: MALVERN PANALYTICAL B.V., Almelo (NL)

(72) Inventors: Petronella Emerentiana Hegeman, Almelo (NL); Gustaaf Christian Brons, Almelo (NL)

(73) Assignee: MALVERN PANALYTICAL B.V., Almelo (NL)

( * ) Notice: Subject to any disclaimer, the term of this patent is extended or adjusted under 35 U.S.C. 154(b) by 0 days.

(21) Appl. No.: 16/295,588

(22) Filed: Mar. 7, 2019

(65) Prior Publication Data

US 2019/0204246 A1 Jul. 4, 2019

Related U.S. Application Data

(63) Continuation of application No. 15/366,632, filed on Dec. 1, 2016.

(51) Int. Cl.
| | | |
|---|---|---|
| *G01N 23/223* | (2006.01) | |
| *B22F 3/105* | (2006.01) | |
| *G21K 1/02* | (2006.01) | |
| *B33Y 10/00* | (2015.01) | |
| *B33Y 80/00* | (2015.01) | |

(52) U.S. Cl.
CPC ......... *G01N 23/223* (2013.01); *B22F 3/1055* (2013.01); *G21K 1/02* (2013.01); *B33Y 10/00* (2014.12); *B33Y 80/00* (2014.12); *G01N 2223/076* (2013.01); *G01N 2223/316* (2013.01); *G01N 2223/507* (2013.01); *G21K 2207/00* (2013.01); *Y02P 10/295* (2015.11)

(58) Field of Classification Search
CPC .................................................. G01N 23/223
See application file for complete search history.

(56) References Cited

U.S. PATENT DOCUMENTS

| | | |
|---|---|---|
| 1,865,441 A | 7/1932 | Mutscheller |
| 4,825,454 A | 4/1989 | Annis |
| 5,682,415 A | 10/1997 | O'Hara |
| 5,892,809 A | 4/1999 | Wittry |
| 5,926,522 A | 7/1999 | McCarthy |
| 7,006,596 B1 | 2/2006 | Janik |
| 7,075,073 B1 | 7/2006 | Janik |

(Continued)

OTHER PUBLICATIONS

Aniouar A. Bzhaumikhov et al: "Polycapillary conic collimator for micro-XRF", Proceedings Optical Diagnostics of Living Cells II, vol. 3444, Nov. 19, 1998 (Nov. 19, 1998), p. 430, XP055457545, us ISSN: 0277-786X, DOI: 10.1117/12.331258 ISBN: 978-1-5106-1324-9.

(Continued)

*Primary Examiner* — Thomas R Artman
(74) *Attorney, Agent, or Firm* — Leason Ellis LLP

(57) ABSTRACT

X ray apparatus includes a sample stage (4) for supporting a sample (6), an X-ray source (2) and an energy dispersive X-ray detector (8). A conical X-ray collimator (10) is provided either between the sample and the X-ray source or between the sample and the energy-dispersive X-ray detector, the conical X-ray collimator including a plurality of truncated cones arranged concentrically around a central axis, the truncated cones having a common apex defining a central measurement spot on the sample.

4 Claims, 3 Drawing Sheets

(56) References Cited

U.S. PATENT DOCUMENTS

| | | | |
|---|---|---|---|
| 7,508,911 B1 | 3/2009 | Lee | |
| 8,462,913 B2 | 6/2013 | Evans | |
| 8,831,175 B2* | 9/2014 | Silver | G21K 1/067 378/149 |
| 8,957,397 B2* | 2/2015 | Malmin | B23H 1/00 250/503.1 |
| 9,330,801 B2* | 5/2016 | Malmin | B23H 1/00 |
| 9,357,973 B2* | 6/2016 | Mattson | G21K 1/10 |
| 9,498,646 B2* | 11/2016 | Bender | A61N 5/1045 |
| 10,121,561 B2 | 11/2018 | Marticke | |
| 2006/0072704 A1* | 4/2006 | Tang | G21K 1/025 378/154 |
| 2008/0170664 A1 | 7/2008 | Kalman | |
| 2008/0192897 A1 | 8/2008 | Piorek et al. | |
| 2009/0074146 A1 | 3/2009 | Lee | |
| 2010/0254514 A1 | 10/2010 | Evans | |
| 2013/0075630 A1* | 3/2013 | Malmin | B23H 1/00 250/505.1 |
| 2013/0188778 A1* | 7/2013 | Silver | G21K 1/067 378/145 |
| 2014/0112431 A1* | 4/2014 | Mattson | G21K 1/10 378/16 |
| 2015/0076375 A1* | 3/2015 | Malmin | B23H 1/00 250/505.1 |
| 2016/0045767 A1* | 2/2016 | Bender | A61N 5/1045 378/149 |
| 2016/0258892 A1 | 9/2016 | Hegeman et al. | |
| 2017/0125133 A1 | 5/2017 | Marticke | |
| 2018/0156745 A1 | 6/2018 | Hegeman | |

OTHER PUBLICATIONS

Stephen Bauters: "Development and applications of Monte Carlo based XRF quantification algorithms for the elemental analysis of cosmic particles", Jan. 1, 2013 (Jan. 1, 2013), XP055458025, DOI: 10.1002/xrs.2479 Retrieved from the Internet: URL:https://lib.ugent.be/fulltxt/RUGOI/002/061/215/RUGOI-002061215 2013 0001AC.pdf [retrieved on Mar. 9, 2018—* pages 23,25 *.

* cited by examiner

CONICAL COLLIMATOR FOR X-RAY MEASUREMENTS

CROSS-REFERENCE TO RELATED PATENT APPLICATIONS

This application is a continuation of U.S. Non-Provisional patent application Ser. No. 15/366,632, filed Dec. 1, 2016, the entire contents of which is incorporated by reference herein as if expressly set forth in its respective entirety herein.

FIELD OF INVENTION

The present invention relates to X-ray fluorescence measurements and apparatus for measuring the same.

BACKGROUND TO THE INVENTION

A variety of different types of X-ray measurements are possible for analysing materials. In an X-ray fluorescence measurement, a beam of X-rays is directed at a sample and the resulting X-rays emitted by the sample are measured by an energy dispersive X-ray detector. Such a detector measures X-ray intensity as a function of energy or equivalently as a function of wavelength.

For homogenous samples, including large crystalline structures, the sample area measured is often not critical. However, some samples such as powder mixtures and others can be inhomogeneous. Alternatively, X-ray measurements may be carried out to measure the inhomogeneity across a sample. In such cases, there is a need to measure X-ray emissions from a small sample spot.

A known approach to such measurements is to use a double pinhole collimator to select an X-ray spot. One option is to place the double pinhole collimator between the X-ray source and the sample. Only X-rays passing through both pin-holes reach the sample so the sample is illuminated only over a small spot. In another approach, a double pinhole collimator is used between the sample and the detector. In this case, only X-rays emitted from a small spot on the sample reach the detector. For example, using a 0.2 mm pinhole and a 0.36 mm pinhole 85.5 mm apart directly in front of a detector 160 mm from the sample a spot size of 0.71 mm diameter can be measured.

The problem with this approach is that the intensity of X-rays from the small spot is limited. Therefore, measurement can take a significant time and result in increased irradiation of the sample.

SUMMARY OF THE INVENTION

According to a first aspect of the invention, there is provided an X-ray fluorescence apparatus, comprising:
a sample stage for supporting a sample;
an X-ray source;
an energy dispersive X-ray detector; and
a conical X-ray collimator provided either between the sample and the X-ray source or between the sample and the energy-dispersive X-ray detector, the conical X-ray collimator including a plurality of truncated cones arranged concentrically around a central axis, the truncated cones having a common apex defining a central measurement spot on the sample.

According to a second aspect of the invention, there is provided a method of making an X-ray measurement, comprising:

directing X-rays from an X-ray source onto a sample;
detecting, using an energy-dispersive X-ray detector, X-rays from the sample;
wherein a conical X-ray collimator is provided either between the sample and the X-ray source or between the sample and the energy-dispersive X-ray detector, the conical X-ray collimator including a plurality of truncated cones arranged concentrically around a central axis, the truncated cones having a common apex defining a central measurement spot on the sample.

The inventors have realised that by using an energy dispersive geometry, in combination with a conical collimator, it is possible to greatly increase the solid angle of the source or detector viewed from the central measurement spot and hence increase the intensity of X-rays. In this way, considerably reduced measurement time can be achieved for measuring a small spot.

Alternatively, the use of a conical collimator may permit a smaller spot to be achieved while still maintaining sufficient X-ray intensity for measurement in a reasonable time scale.

The conical collimator may subtend a solid angle of more than 0.1 mSr. Such a conical collimator subtends a solid angle much greater than the solid angle subtended by a double pinhole collimator which may have a solid angle of order 1 μSr. This means that where the conical collimator is placed between the sample and the detector, a greater detector area may be used to detect X-rays. The approach would not work with angle dispersive measurements, since the greater detector area for a single spot would correspond to a range of diffraction angles preventing accurate measurements. This difficulty is avoided using an energy dispersive technique.

The conical collimator may in particular be integrally formed, i.e. be a single piece without joins or welds. Such a collimator may be formed, for example, by direct metal sintering.

The conical collimator may be of refractive metal, such as tungsten or molybdenum. Such a heavy metal provides for good collimation even for thin samples.

In the past, manufacture of such a conical collimator in a single piece and/or of heavy metal would not have been technically possible. The inventors have realised however that modern manufacturing techniques makes it possible to manufacture a refractive metal conical collimator in a single piece which can define a highly collimated central measurement spot. In other words, the inventors have realised that improved collimation can be achieved using the conical collimator as proposed herein.

Where the conical collimator is placed between the sample and the detector, providing a range of output solid angle, there is a need to avoid excessive collimation of the source X-ray beam incident on the sample since the variation of angles of incidence of the beam should at least equal the variation of angles of output across the conical X-ray collimator.

Similarly, where the conical collimator is placed between the sample and the source, there is again a need to avoid excessive collimation between the sample and the detector.

The conical X-ray collimator may define a spot at the sample stage of lateral dimension no more than 1 mm, preferably not more than 0.5 mm, further preferably not more than 0.2 mm.

The conical collimator may subtend a solid angle of 0.1 mSr to 10 mSr. This is much greater than can be obtained in a double pinhole configuration in a high resolution X-ray fluorescence apparatus.

The conical collimator may include at least 4 concentric truncated cones supported by a plurality of radial supports.

Each truncated cone may be a sheet having a thickness of 40 μm to 200 μm.

The spacing between adjacent truncated cones may be in the range 50 μm to 250 μm.

Conical collimators suitable for use in X-ray fluorescence apparatus are not commercially available and are far from trivial to manufacture. Accordingly, in a third aspect of the invention, there is provided a method of manufacturing a collimator adapted to be mounted in front of an energy dispersive X-ray detector, the method comprising:

using a direct metal laser sintering process to form a conical collimator of refractive metal;

carrying out a further etch process to etch the refractive metal and etch away small particles of the refractive metal.

The inventors have realised that direct metal laser sintering makes it possible to manufacture the complex structure needed to form a conical collimator in this application. Further, it is possible to manufacture such a collimator in a way that allows for integration into existing X-ray fluorescence apparatus.

By using a conical collimator, greatly increased X-ray intensity can be achieved during measurement than with a double pin-hole collimator.

There are a significant number of processes that could be used to manufacture shapes and in particular a number of additive and subtractive manufacturing metals are available.

Preferably, the reactive metal is titanium or molybdenum.

BRIEF DESCRIPTION OF THE DRAWINGS

An example of the invention will now be described with reference to the accompanying diagrams, in which.

DETAILED DESCRIPTION

Figure 1:
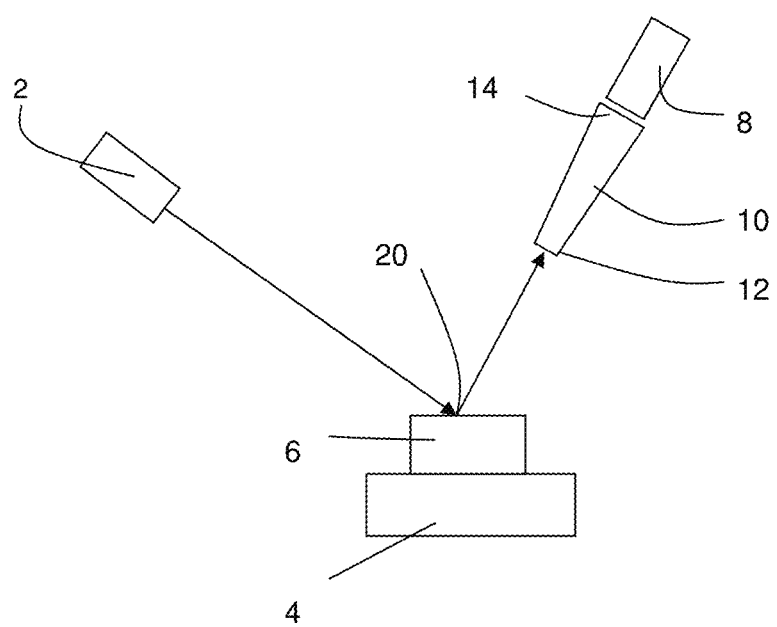
FIG. 1 is a schematic diagram of X-ray florescence apparatus according to the invention.

Referring to FIG. 1, X-ray apparatus includes an X-ray source 2, a sample stage 4 shown with a sample 6 and an energy dispersive X-ray detector 8. Such an arrangement is used in particular for X-ray fluorescence.

Figure 2:
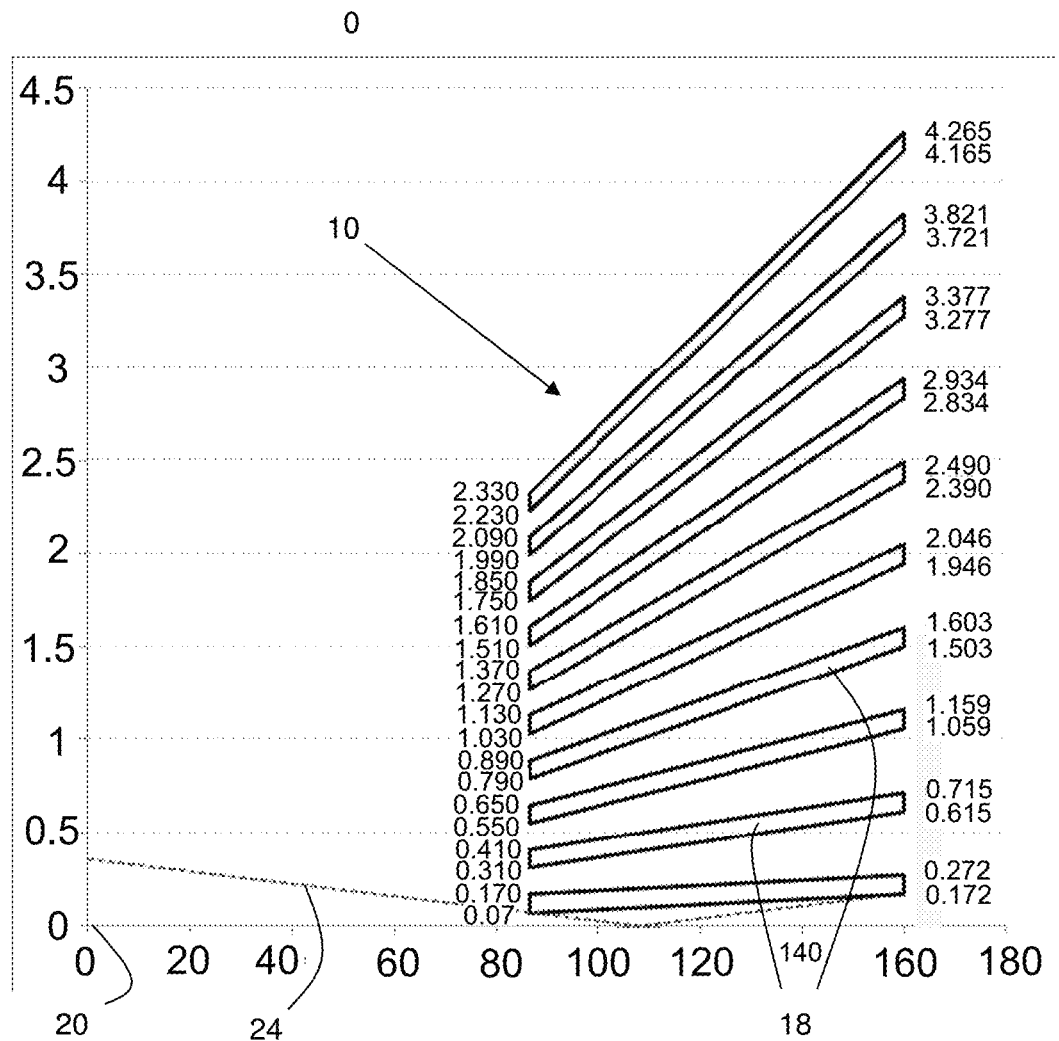
FIG. 2 is a schematic diagram of the conical collimator of FIG. 1.
Figure 3:
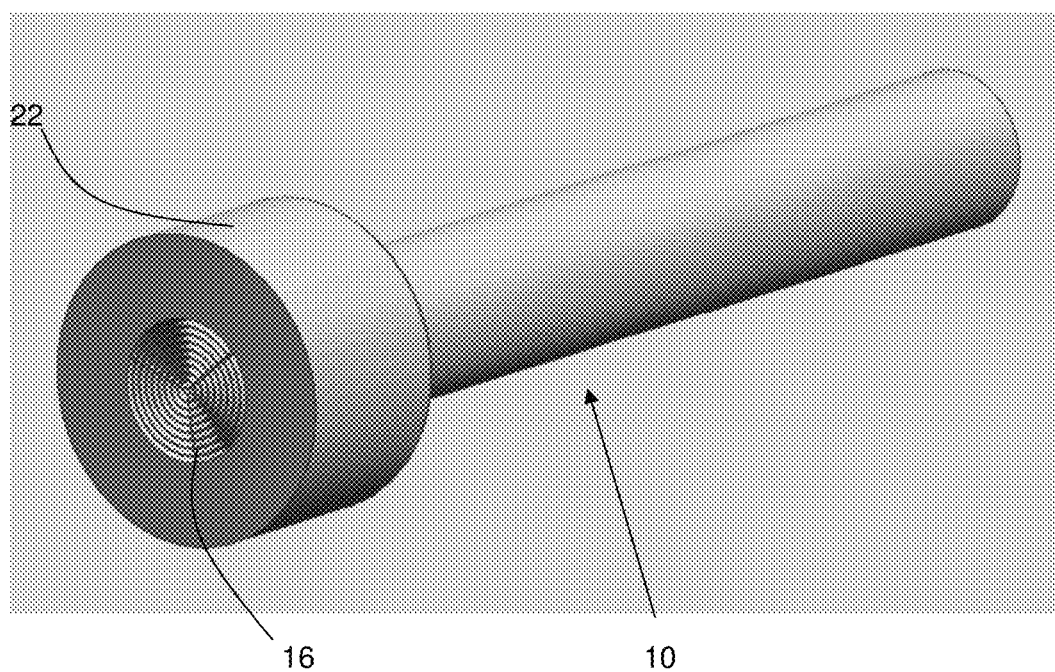
FIG. 3 is a perspective view of the conical collimator of FIG. 2.

A collimator 10 is mounted in front of the energy dispersive X-ray detector 8 extending a central end 12 close to the sample stage to an outer end 14 adjacent to the detector as illustrated in more detail in FIG. 2. FIG. 3 shows a perspective view of the collimator 10.

The collimator 10 is made of a plurality of truncated cones 18 each formed of a metal, in the example the refractive metal tungsten. Note that FIG. 2 shows a section through the collimator and the space between the collimator and the focal spot 20 as well as the vanes 18 in a graphical format in which the vertical axis is highly exaggerated compared with the horizontal axis—the scales on both axes are in mm.

The sheets are a nominal 0.10 mm thick. Each sheet is formed into a truncated cone 18 having as its centre a focal spot 20 located such that it is at the surface of sample 6 on the sample stage.

The spacing between the truncated cones varies along the length of the collimator 10 and starts at a nominal 0.14 mm at the central end 2 and expands to a nominal 0.344 mm at the outer end 14.

A plurality of vanes 16 (visible in FIG. 3) support the truncated cones 18. In the example, the vanes 16 extend the full length of the collimator 10. Note from FIG. 3 that the outer surface of the conical collimator 10 need not itself be conical—what is important is that the plurality of truncated cones are conical. The conical collimator may include a flange 22 that is used for locating the conical collimator 10 correctly.

Although this description of a conical collimator refers to the separate elements of the conical collimator these elements are not in this embodiment individual separate parts but the conical collimator is integrally formed to be a single piece.

It will be appreciated that FIG. 1 is highly schematic and that other components such as a housing, controllers, additional ports, and many others known to those skilled in the art may also be present.

Such collimators 10 may be manufactured by a direct metal laser sintering process as will now be described.

Direct metal laser sintering is an additive manufacturing method by which a product is built up layer by layer and not formed by milling from a solid bloc. A thin layer of powder is applied to a part-formed product on a stage and a laser beam is used to fuse the powder at points defined from a computer aided design (CAD) file. This forms material at these points.

The stage is then lowered and a new layer is applied by repeating these steps.

A commercially available piece of equipment, an EOS M270, is used for the laser sintering.

In order to form a collimator as described above, fine tungsten powder was used. The layer thickness for the formation of the product was set to be in the range 10 μm to 50 μm. A nitrogen atmosphere was used and the process started on a stainless steel stage.

After forming the collimator 10, a further etch process is carried out to remove any tungsten particles remaining. Any etchant capable of etching tungsten may be used, either a dry or a wet etch. This also reduces the thickness of the sheets of the truncated cones 18.

Accordingly, in the collimator, the actual thickness of each sheet is 0.090 mm, the spacing at the central end 12 is 0.150 mm and the spacing at the outer end 14 is 0.354 mm. In another embodiment, with less etching, the actual thickness of each sheet is 0.095 mm, the spacing at the central end 12 is 0.145 mm and the spacing at the outer end 14 is 0.349 mm.

In use, X-rays from the X-ray source 2 are incident on the sample 6. This causes fluorescence, i.e. the emission of secondary X-rays from the sample.

Only X-rays from a small focal spot 20 on the surface of the sample are able to pass through the conical collimator 10 and arrive at the X-ray detector 8. Other X-rays such as illustrative X-ray 24 are absorbed on the cones 18 of the collimator. This can cause some secondary re-emission, but this can be taken into account.

Calculations have been carried out to compare the spot size and flux achieved with a double pinhole collimator and the conical collimator.

The comparative example is a double pinhole collimator with a 0.200 mm diameter pinhole at 74.5 mm from the sample and a 0.360 mm pinhole at 160 mm from the focal spot of the sample.

The examples use a conical collimator 10 as described above, with 0.100 mm, 0.095 mm or 0.090 mm thick truncated cones extending from 86.6 mm from the focal spot 20 of the sample to 160 mm from the focal spot 20 of the sample. Accordingly, the conical collimator 10 extends for a similar distance to the double pinhole collimator.

Table 1 tabulates the ratio of intensity (kilo counts per second (kcps)) when measuring four samples—a Cu disk, a sample labelled "MBH" of aluminium copper alloy, AlCu, a sample of manganese oxide, $MnO_2$, and a Mo disk. The intensity ratio is the ratio of counts, in each case measured for 60 seconds, using a conical collimator compared with the count using a double pinhole collimator. As can be seen from the table, the increase in intensity using the conical collimator is a significant increase—a factor in the range 150 to 165 for these samples.

TABLE 1

| Sample | Time (s) | Intensity ratio increase |
|---|---|---|
| Cu | 60 | 152.4 |
| MBH | 60 | 159.4 |
| $MnO_2$ | 60 | 154.6 |
| Mo | 60 | 16.4 |

Thus, it will be seen that a substantial advantage that was not previously achievable is achieved using the conical collimator approach described here.

Those skilled in the art will realise that alternatives to this arrangement are possible.

Instead of mounting the conical collimator 10 in front of the detector, the conical collimator may also be mounted between the source 2 and the sample stage 4. This alternative approach has the benefit of only irradiating the focal spot 20 which may be of benefit for applications where it is important to minimise X-ray irradiation of the sample.

Instead of tungsten as the material of the conical collimator, alternative refractive metals may also be used, for example molybdenum. Indeed, it may be convenient to provide conical collimators of different metals for use with different materials.

The thickness of the truncated cones of the conical collimator may be varied depending on manufacturing method and the requirements of any particular application.

The three dimensional design, including the length and width, may also be varied to fit the conical collimator in alternative designs of X-ray fluorescence apparatus. In some designs, the conical collimator may be integrated into a housing also containing the energy dispersive X-ray detector so that the conical collimator and X-ray detector may form a single unit.

The spot size achieved by the conical collimator may also vary—for some applications a 0.5 mm diameter spot may be appropriate, for other applications 0.2 mm or 1 mm may be suitable. Where it is not important to locate only a small region of the sample, a spot diameter of 2 mm or even 4 mm may be used.

The invention claimed is:

1. A method of manufacture of a conical collimator for an X-ray fluorescence apparatus, the method comprising:
    using a direct metal laser sintering process to form a conical collimator of refractive metal, the conical collimator including a plurality of truncated cones arranged concentrically around a central axis, the truncated cones having a common apex defining a central measurement spot on the sample, for collimating X-rays; and
    carrying out a further etch process to etch the refractive metal and etch away small particles of the refractive metal.

2. The method of claim 1, wherein the conical collimator includes at least 4 concentric truncated cones supported by a plurality of radial supports.

3. The method of claim 2, wherein each truncated cone is formed of a sheet having a thickness of 40 μm to 200 μm.

4. The method of claim 3, wherein the spacing between adjacent truncated cones at the closest point is in the range 50 μm to 250 μm.

* * * * *